US008571178B2

(12) United States Patent
Sendai

(10) Patent No.: US 8,571,178 B2
(45) Date of Patent: Oct. 29, 2013

(54) RADIATION IMAGING APPARATUS AND IMAGING CONTROL DEVICE CONTROLLING A FILTER BASED ON SUBJECT INFORMATION

(75) Inventor: Tomonari Sendai, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 268 days.

(21) Appl. No.: 12/889,945

(22) Filed: Sep. 24, 2010

(65) Prior Publication Data
US 2011/0075810 A1    Mar. 31, 2011

(30) Foreign Application Priority Data

Sep. 25, 2009   (JP) ................................. 2009-220289

(51) Int. Cl.
*H05G 1/64* (2006.01)
*G21K 3/00* (2006.01)

(52) U.S. Cl.
USPC ......... 378/98.9; 378/95; 378/98.11; 378/157; 378/158

(58) Field of Classification Search
USPC .......... 378/5, 8, 16, 98.9, 98.11, 156–159, 95
See application file for complete search history.

(56) References Cited

U.S. PATENT DOCUMENTS

| 4,445,226 A * | 4/1984 | Brody ........................... 378/98.9 |
| 4,482,918 A | 11/1984 | Keyes et al. |
| 4,686,695 A * | 8/1987 | Macovski ..................... 378/146 |
| 5,107,529 A | 4/1992 | Boone |
| 5,204,888 A * | 4/1993 | Tamegai et al. ................. 378/53 |
| 5,661,774 A * | 8/1997 | Gordon et al. ................ 378/101 |
| 6,226,352 B1 * | 5/2001 | Salb ............................. 378/98.9 |
| 6,269,140 B1 * | 7/2001 | Takagi et al. ..................... 378/8 |
| 6,298,111 B1 * | 10/2001 | Ozaki ............................... 378/8 |
| 6,507,639 B1 * | 1/2003 | Popescu ....................... 378/108 |
| 6,560,309 B1 * | 5/2003 | Becker et al. ..................... 378/8 |
| 6,574,500 B2 * | 6/2003 | Keren .......................... 600/431 |
| 6,614,878 B2 * | 9/2003 | Bogatu et al. ................ 378/158 |

(Continued)

FOREIGN PATENT DOCUMENTS

| JP | 60-005126 A | 1/1985 |
| JP | 61-095338 A | 5/1986 |

(Continued)

OTHER PUBLICATIONS

Search Report issued in EP 10178996.4 dated Mar. 12, 2012, 7 pages.

(Continued)

*Primary Examiner* — Allen C. Ho
(74) *Attorney, Agent, or Firm* — Sughrue Mion, PLLC

(57) ABSTRACT

A motor controller determines a drive speed of a motor for driving a filter such that an area shifting cycle of the filter synchronizes with a cardiac cycle. The filter starts to rotate before radiation emission, and continues to rotate at a constant speed during two successive radiation emissions. An emission controller controls timing of two emissions in accordance with a phase of the filter. The area shifting cycle of the filter and the cardiac cycle are previously synchronized, and thus a high-performance filter switching device for switching or shifting the filter in synchronization with the emission timing becomes unnecessary. Adjusting the area shifting cycle of the filter in accordance with the cardiac cycle realizes two radiation emissions in two successive cardiac cycles. As a result, an exposure time is shortened.

7 Claims, 12 Drawing Sheets

(56) References Cited

U.S. PATENT DOCUMENTS

| | | | |
|---|---|---|---|
| 6,633,627 B2 * | 10/2003 | Horiuchi | 378/156 |
| 6,643,536 B2 | 11/2003 | Nicolas et al. | |
| 7,116,749 B2 * | 10/2006 | Besson | 378/16 |
| 7,120,222 B2 * | 10/2006 | Hoffman | 378/5 |
| 7,158,611 B2 * | 1/2007 | Heismann et al. | 378/98.9 |
| 7,330,535 B2 * | 2/2008 | Arenson et al. | 378/158 |
| 7,463,715 B2 * | 12/2008 | Spahn | 378/98.12 |
| 7,616,730 B2 * | 11/2009 | Flohr | 378/8 |
| 7,636,413 B2 | 12/2009 | Toth | |
| 7,649,981 B2 * | 1/2010 | Seppi et al. | 378/158 |
| 7,668,585 B2 * | 2/2010 | Green | 600/428 |
| 8,218,728 B2 * | 7/2012 | Karch | 378/98.11 |
| 2002/0141624 A1 | 10/2002 | Gil et al. | |

FOREIGN PATENT DOCUMENTS

| | | |
|---|---|---|
| JP | 2-63439 A | 3/1990 |
| JP | 10-192273 A | 7/1998 |
| JP | 2002-325756 A | 11/2002 |
| JP | 2003-210442 A | 7/2003 |
| JP | 2003-325504 A | 11/2003 |
| JP | 2009-000293 A | 1/2009 |
| JP | 2009-160100 A | 7/2009 |

OTHER PUBLICATIONS

Notification of Reasons for Refusal, dated Mar. 27, 2013, issued in corresponding JP Application No. 2009-220289, 4 pages in English and Japanese.

* cited by examiner $S1 = \alpha 1 \times H - \beta 1 \times L + B1$　　　$S2 = \alpha 2 \times H - \beta 2 \times L + B2$

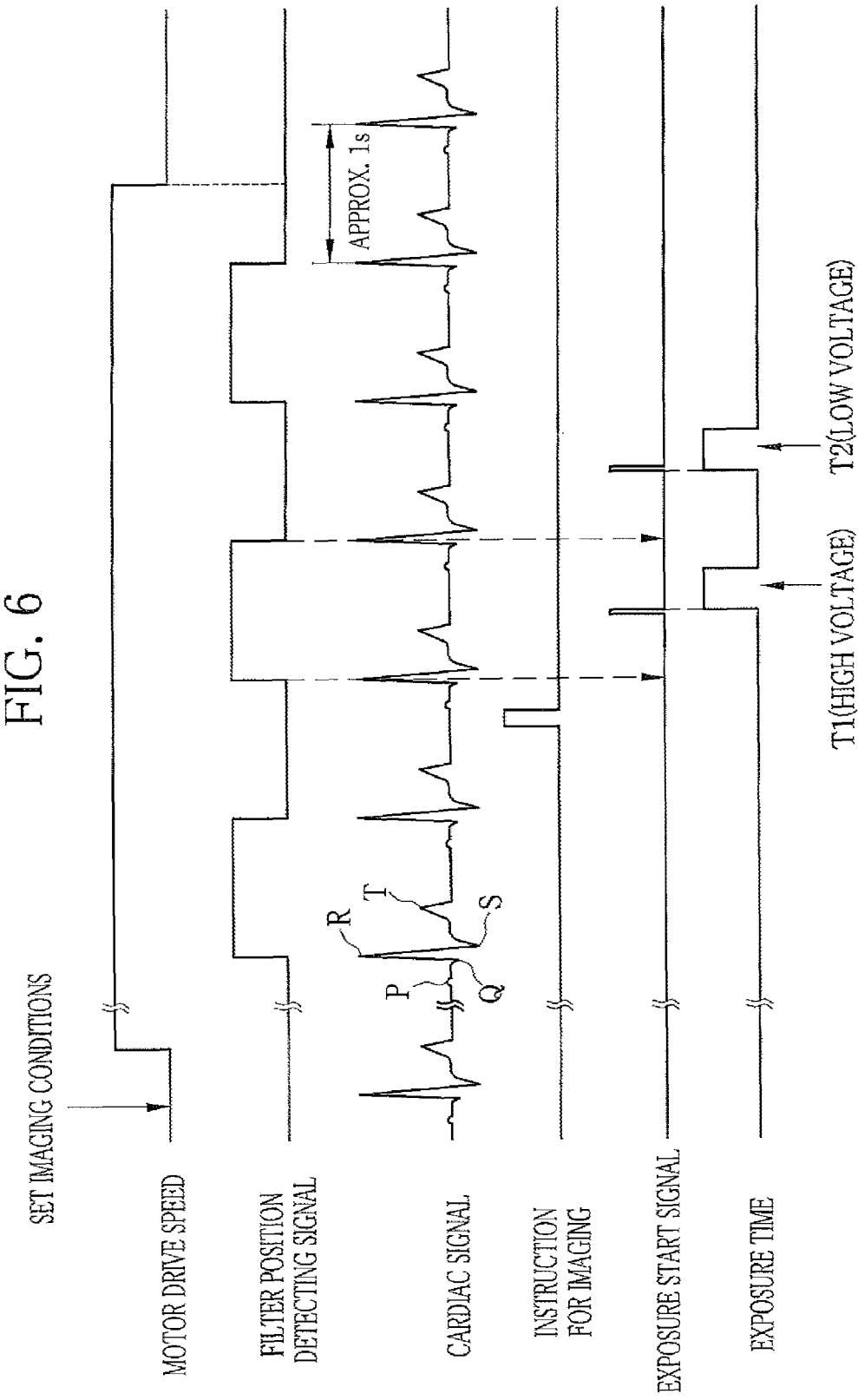

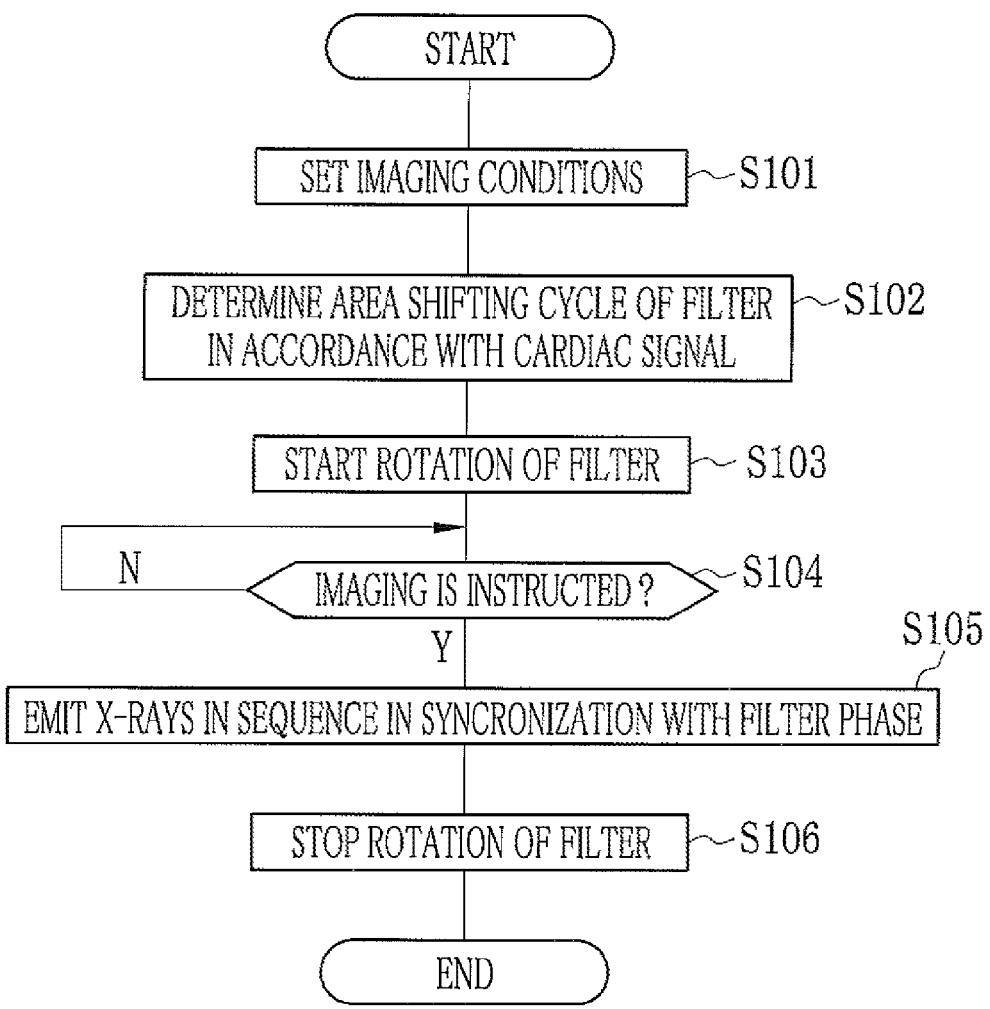

CARDIAC SIGNAL

RESPIRATORY SIGNAL

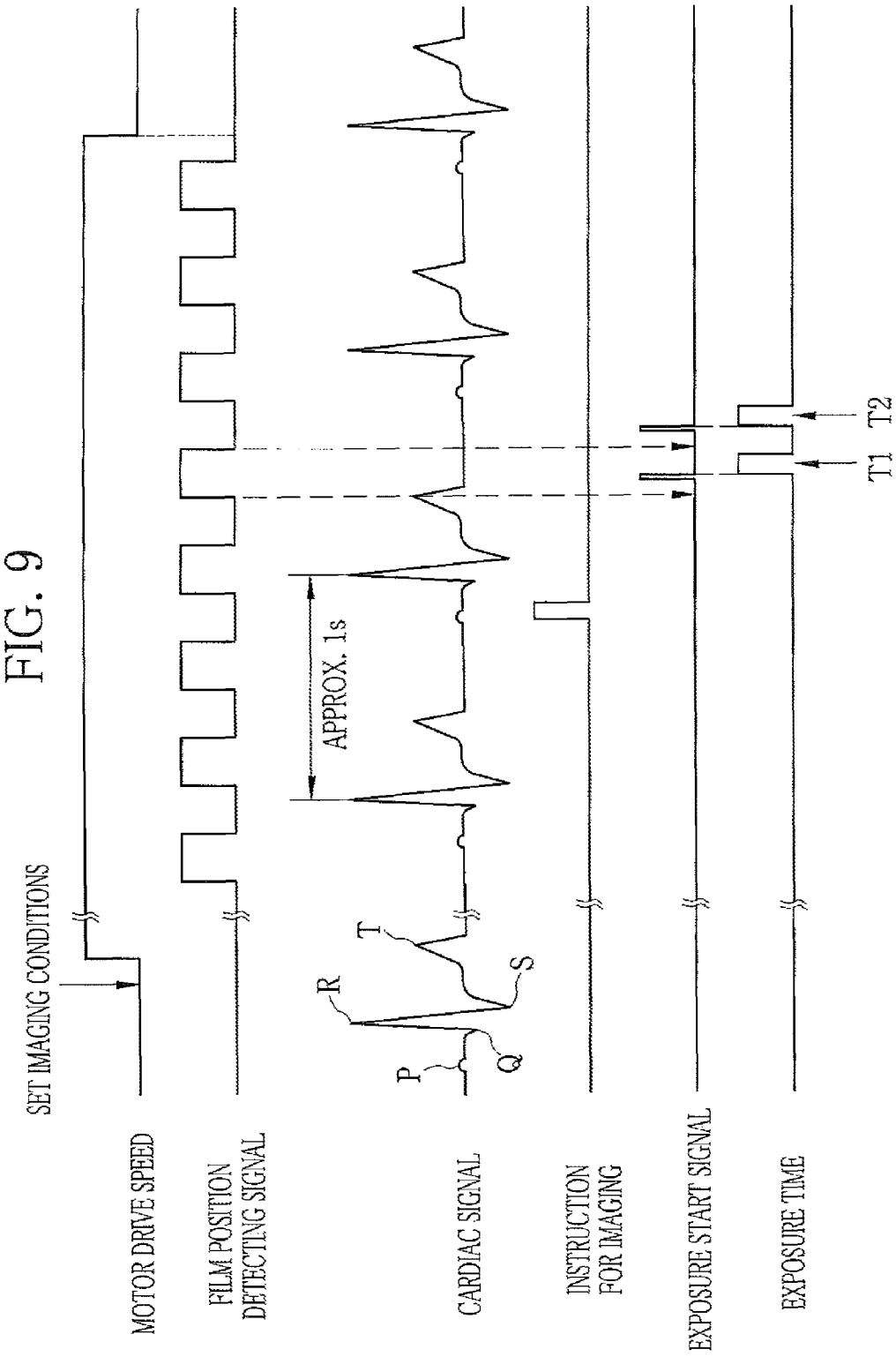

| DOSE | COMBINATION 1 | COMBINATION 2 | COMBINATION 3 |
|---|---|---|---|
| 4mAs | 100mA×0.04s | 200mA×0.02s | 400mA×0.01s |
| 8mAs | 100mA×0.08s | 200mA×0.04s | 400mA×0.02s |
| ⋮ | ⋮ | ⋮ | ⋮ |

RADIATION IMAGING APPARATUS AND IMAGING CONTROL DEVICE CONTROLLING A FILTER BASED ON SUBJECT INFORMATION

FIELD OF THE INVENTION

The present invention relates to a radiation imaging apparatus for capturing multiple radiation images used in energy subtraction and an imaging control device for performing energy subtraction imaging.

BACKGROUND OF THE INVENTION

In the field of medical radiation imaging, energy subtraction technique is known. With the energy subtraction technique, images in which specific tissue is enhanced, e.g. soft tissue images and bone part images are obtained. A soft tissue image representing soft tissue, e.g. lungs and esophagus, is obtained by removing a component of bones, e.g. ribs and the backbone, from an image of a subject or patient. On the other hand, a bone part image representing the component of bones is obtained by removing a component of the soft tissue.

The energy subtraction technique is based on the fact that tissue such as bones or the soft tissue has specific radiation energy absorption properties. Two kinds of radiations different in energy distribution are emitted onto the same object of interest to obtain two kinds of raw images, namely, a high energy image and a low energy image, for energy subtraction. These two raw images are properly weighted, and then a pixel value of one of the images is subtracted from a pixel value of the other image to obtain a difference. Thus, a subtracted image in which images of specific tissues are enhanced, e.g. a soft tissue image or a bone part image, is obtained.

A two-shot method in which radiations of two different energy levels are emitted in sequence to a subject is known as one of methods to obtain two raw images, a high energy image and a low energy image (see, for example, U.S. Pat. No. 4,482,918 corresponding to Japanese Patent Laid-Open Publication No. 2-063439). To obtain the radiations of two different energy levels, a radiation tube voltage of the radiation source may be changed, for example. When a high radiation tube voltage is applied to the radiation source, the radiation source generates high-energy radiation having an energy distribution with a larger high energy component. When a low radiation tube voltage is applied to the radiation source, the radiation source generates low-energy radiation having an energy distribution with a larger low energy component.

The energy distribution of low-energy radiation and the energy distribution of high-energy radiation partly overlap with each other. Since the energy subtraction technique uses a difference between the energy components of the two kinds of radiations, a smaller overlap in the energy components, which enables high energy separation performance, is preferable. To improve energy separation between the high-energy radiation and the low-energy radiation, a low energy component of the high-energy radiation is cut or filtered out during the emission of high energy radiation (see Japanese Patent Laid-Open Publication No. 2003-210442).

For an imaging apparatus of Japanese Patent Laid-Open Publication No. 2003-210442, a filter has a disc-shape and rotates at a constant speed. The filter has a filter area formed on a semicircular area of the disc. The filter area cuts the low energy component of radiation. Rotating the filter at a constant speed allows the filter area to be inserted and retracted from a path of radiation at a fixed cycle. Two successive radiation emissions are synchronized with the phases of the filter, respectively. Specifically, high-energy radiation is emitted while the filter area is inserted into the path of the radiation, and low-energy radiation is emitted while the filter area is retracted from the path. In other words, the imaging apparatus of Japanese Patent Laid-Open Publication No. 2003-210442 controls the emission timing in synchronization with the fixed area shifting cycle or shift cycle of the filter.

On the other hand, an imaging apparatus of U.S. Pat. No. 7,636,413 (corresponding to Japanese Patent Laid-Open Publication No. 2003-325504) discloses a filter composed of four rectangular filter plates each having a different filter area. The four filter plates are attached to a rotary hub at 90-degree intervals. In accordance with a switch pulse which is outputted in synchronization with the exposure start signal, the rotary hub rotates by 90 degrees to insert the filter plates into the radiation path in sequence. Unlike the imaging apparatus of Japanese Patent Laid-Open Publication No. 2003-210442, the area shifting cycle of the filter is not fixed in the imaging apparatus of U.S. Pat. No. 7,636,413. The switch timing or positioning of the filter plates is controlled such that the filter plates are rotated or shifted in accordance with the emission timing.

It is known that the two-shot method has problems, such as to improve energy separation performance and to reduce motion artifacts or virtual images caused by body motion. For example, for chest imaging, a motion artifact caused by a heartbeat is generated in a subtracted image, which is obtained by energy subtraction processes, when cardiac phases of the two raw images for the energy subtraction do not coincide with each other, for example, the first emission or first exposure is performed during diastole or relaxation phase of a heartbeat, and the second emission or second exposure is performed during systole or contraction phase. For an imaging technique to reduce motion artifacts, cardiac cycles of a patient are monitored to perform two successive emissions at the same cardiac phases, respectively (see U.S. Pat. No. 6,643,536, corresponding to Japanese Patent Laid-Open Publication No. 2002-325756).

For imaging using the energy subtraction, U.S. Pat. No. 4,482,918, Japanese Patent Laid-Open Publication No. 2003-210442, and U.S. Pat. No. 7,636,413 disclose techniques in which two successive emissions and filter switch timings are synchronized, respectively, to improve energy separation performance. On the other hand, U.S. Pat. No. 6,643,536 discloses techniques to perform two successive emissions at the same cardiac phases, respectively, to reduce the motion artifact. However, none of the above discloses the technique capable of improving the energy separation performance and reducing the motion artifact at the same time.

To improve energy separation performance and reduce motion artifacts at the same time, an applicant contemplates to combine the techniques disclosed in U.S. Pat. No. 6,643,536 and the techniques disclosed in U.S. Pat. No. 4,482,918, Japanese Patent Laid-Open Publication No. 2003-210442, and U.S. Pat. No. 7,636,413. That is, two successive emission timings and the filter switch timings are synchronized respectively, while the two successive emissions are performed at the same cardiac phases, respectively.

Cardiac cycles vary among individuals, and even vary within the same person. If the filter is switched or shifted at a fixed area shifting cycle, and when the area shifting cycle and the cardiac cycle are asynchronous, an operator needs to wait for the timing at which the filter phase and the cardiac phase coincide with each other. As a result, imaging time becomes long.

For example, when the area shifting cycle of the filter and the cardiac cycle are synchronous, two radiation emissions can be performed at the same cardiac phases, respectively. As a result, the imaging time becomes short. On the other hand, when the area shifting cycle of the filter and the cardiac cycle are asynchronous, even if the first radiation emission is performed at timing in which the filter phase and the cardiac cycle coincide with each other, the area shifting cycle of the filter do not synchronize with subsequent cardiac cycle. In this case, the operator needs to wait for the timing at which the filter phase and the cardiac phase coincide with each other again.

Body motion, for example, heart motion or lung motion of a patient occurs due to breathing in addition to heartbeats. To reduce the motion artifact caused by breathing, a patient is often asked to hold his or her breath during the imaging. A long time interval between the first and second radiation emissions extends the imaging time. As a result, the patient needs to hold his or her breath for a long time, which increases physical burdens of the patient.

The imaging time can be shortened with the use of the imaging apparatus disclosed in U.S. Pat. No. 7,636,413. This imaging apparatus uses a filter switching device capable of synchronizing the insert timing of the filter and the emission timing. It is unnecessary to wait for the timing in which the filter phase and the cardiac phase coincide with each other. Thus, the imaging time becomes short.

However, the filter switching device shown in FIG. 7 of U.S. Pat. No. 7,636,413 generates switch pulses in synchronization with each exposure start signal to switch or shift the filter during the radiation emission. Accordingly, the filter is accelerated or decelerated in a short time to place the filter in the intended position, which requires a motor with high responsiveness and the motor control with high precision. As a result, the device cost significantly increases.

SUMMARY OF THE INVENTION

An object of the present invention is to provide a radiation imaging apparatus for performing energy subtraction imaging in a short time and an imaging control device capable of controlling this energy subtraction imaging.

Another object of the present invention is to provide a radiation imaging apparatus and an imaging control device at low cost.

Still another object of the present invention is to provide a radiation imaging apparatus and an imaging control device with high separation performance for radiation energy.

In order to achieve the above and other objects, the radiation imaging apparatus of the present invention includes a radiation source, a filter, a cycle determining section, and a driver. The radiation source performs multiple radiation emissions to a subject. The filter has at least one filter area for changing energy distribution of radiation in at least one of the radiation emissions. The filter periodically shifts between an inserted state in which the filter area is inserted in a path of the radiation and a retracted state in which the filter area is retracted from the path. The cycle determining section determines a shift cycle of the filter for shifting the filter area between the inserted state and the retracted state based on subject information. The driver drives the filter to shift at the determined shift cycle. The driver drives the filter to start shifting before a start of the first radiation emission and to shift until an end of the last radiation emission after the first radiation emission.

It is preferable that the radiation imaging apparatus further includes an emission controller for outputting a signal for starting the radiation emission to the radiation source to control emission timing of the radiation.

It is preferable that the subject information is cardiac cycle information or respiration information of the subject, and the radiation imaging apparatus further includes a signal detector for detecting at least one of a cardiac signal indicating a state of the cardiac cycle information and a respiratory signal indicating a state of the respiration information.

It is preferable that the cycle determining section determines the shift cycle so as to be in synchronization with the cardiac cycle information or the respiration information.

It is preferable that the cycle determining section determines the shift cycle so as to be in synchronization with the cardiac cycle information, and the emission controller synchronizes the emission timing with a phase of the respiration based on the respiratory signal.

It is preferable that the radiation imaging apparatus further includes a filter phase detector for detecting a phase of the filter, and the emission controller synchronizes the emission timing with the phase of the filter.

It is preferable that the subject information is body thickness of the subject, and the cycle determining section determines the shift cycle in accordance with a maximum exposure time determined based on the body thickness.

It is preferable that the filter includes multiple filter areas and the multiple filter areas are selectively inserted in sequence into the path.

It is preferable that the filter includes multiple filters each having at least one filter area, and the filters are selectably used.

It is preferable that each of the filters is individually rotatable, and arranged to be insertable into the path, and has a transmission area for retracting the filter area of the filter when the filter area of another filter is inserted in the path.

The imaging control device for controlling the radiation source and the filter of the present invention includes a cycle determining section and a controller. The cycle determining section determines a shift cycle of the filter for shifting the filter area between the inserted state and the retracted state based on subject information. The controller controls a driver for driving the filter. The controller controls the driver to shift the filter at the determined shift cycle by starting before a start of the first radiation emission and until an end of the last radiation emission after the first radiation emission.

According to the present invention, the shift cycle of the filter is previously determined based on the subject information. The filter starts to shift at the determined shift cycle before the start of the first radiation emission and continues to shift until the end of the last radiation emission after the first radiation emission. Thus, the radiation imaging apparatus and the imaging control device capable of performing the energy subtraction imaging in a short time at low cost, and with high separation performance for radiation energy are provided.

In the present invention, the filter rotates at a constant speed during the energy subtraction imaging, namely, before the start until the end of the radiation emissions. Accordingly, the present invention eliminates the use of a device such as a conventional high-performance filter switching device which inputs a pulse in accordance with the exposure start signal outputted during imaging to switch filters as described in U.S. Pat. No. 7,636,413. As a result, no additional device cost is incurred.

The shift cycle of the filter is determined based on, for example, the cardiac cycle information which is the subject information, allowing two radiation emissions within two successive heartbeats. As a result, the energy subtraction imaging is performed in a short time, reducing physical burdens of the subject.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein:

FIG. 6 is a timing chart of a filter position detecting signal, a cardiac signal, and exposure timings;

FIG. 7 is a flow chart showing image capture steps;

FIG. 9 is a timing chart illustrating two radiation exposures performed in a single cardiac cycle;

DESCRIPTION OF THE PREFERRED EMBODIMENTS

First Embodiment

Figure 1:
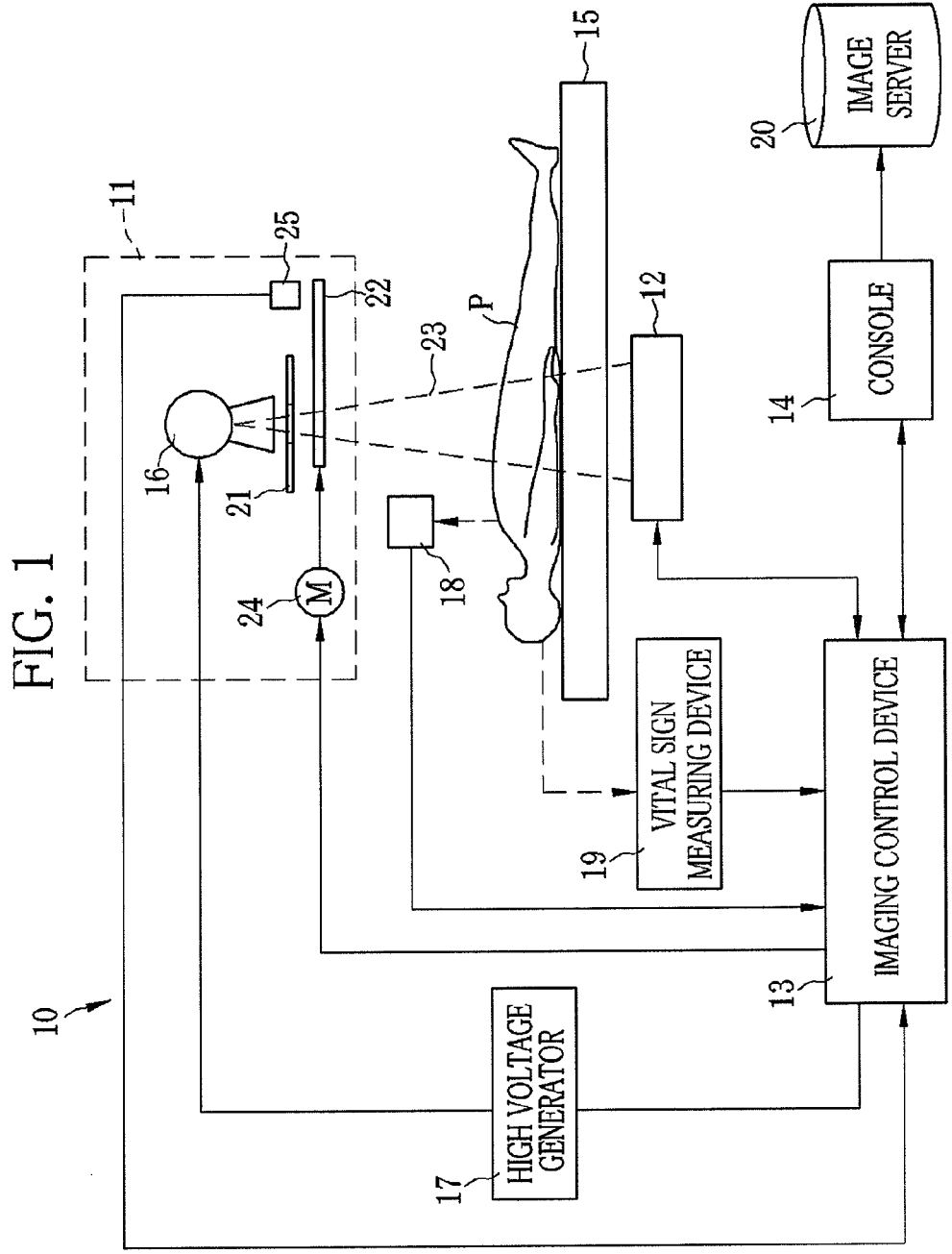
FIG. 1 is a schematic diagram of a radiation imaging apparatus.

In FIG. 1, a radiation imaging apparatus 10 is composed of a radiation source 11 for generating and emitting radiation, a radiation image detector 12 for receiving the radiation passed through a subject P to detect a radiation image, an imaging control device 13 for controlling the radiation source 11 and the radiation image detector 12, and a console 14 for inputting operation instructions such as exposure conditions and instructions for imaging to the imaging control device 13. The radiation imaging apparatus 10 is, for example, a laying-type imaging apparatus for capturing images of the subject P laid down on a patient table 15.

The radiation source 11 is provided with a radiation tube, for example, an X-ray tube 16 having a cathode filament and an anode target. A high voltage is applied between the cathode and the anode, so that thermal electrons released from the filament hit the target. Thus, X-ray is generated. The target has a disc-like shape, and rotates while the filament releases the thermal electrons. Rotating the target increases a target area which thermal electrons hit. As a result, a thermal capacity of the target is increased, which reduces thermal damage. For example, molybdenum (Mo) and tungsten (w) are used as materials of the target.

Changing the X-ray tube voltage (unit: kV) changes the energy distribution of X-ray emitted from the radiation source 11. An amount of X-ray emission (hereinafter referred to as emission amount or dose) is defined by the product (unit: mAs) of an X-ray tube current (unit: mA) and an exposure time (unit: second or abbreviated as "s"). If the dose is unchanged, the exposure time increases as the X-ray tube current decreases, and the exposure time decreases as the X-ray tube current increases. A voltage generated by a high voltage generator 17 is applied to the radiation source 11.

The radiation imaging apparatus 10 has a function to perform energy subtraction imaging. To perform energy subtraction imaging, the radiation source 11 emits X-rays at two wavelengths, high-energy X-ray and low-energy X-ray, in sequence. The high-energy X-ray has an energy distribution in which peak energy and average energy are high. The low-energy X-ray has an energy distribution in which peak energy and average energy are low compared to the high-energy X-ray.

The imaging control device 13 sends an exposure start signal, the maximum exposure time, an exposure stop signal, and control signals to the high voltage generator 17 in order to control the radiation source 11. The exposure start signal defines exposure timing of the radiation source 11. The maximum exposure time is determined in accordance with imaging conditions. The exposure stop signal causes radiation source 11 to stop the exposure when the exposure amount reaches a predetermined value. The control signals control an X-ray tube voltage, an X-ray tube current, and the like. When an instruction for energy subtraction imaging is inputted through the console 14, the imaging control device 13 sends two types of control signals, the control signal for high voltage and the control signal for low voltage, to the high voltage generator 17 so as to allow the radiation source 11 to emit the high-energy X-ray and the low-energy X-ray in sequence.

The imaging control device 13 monitors a status of the voltage generated by the high voltage generator 17. The imaging control device 13 judges that the voltage is in an anomalous status when the generated voltage does not reach its intended value or the voltage largely fluctuates. When the imaging control device 13 detects a voltage anomaly, the imaging control device 13 controls the radiation source 11 to stop the exposure, and raises an alarm indicating the voltage anomaly.

The radiation image detector 12 is a flat panel detector having a photoconductive layer, a capacitor, and a detector-element array on an insulation substrate such as a glass substrate. The photoconductive layer photoelectrically converts X-ray into signal charge. The capacitor stores the signal charge. The detector-element array has multiple detector elements (pixels) arranged in matrix and composed of TFTs (thin film transistors) for reading the stored signal charge. The radiation image detector 12 turns off the TFTs during the X-ray emission and performs signal charge accumulation. After the X-ray emission is ended, the radiation image detector 12 turns on the TFTs to read the accumulated signal charge.

The signal charge in each pixel is read by the TFT, and then converted into digital image data by an A/D converter (not shown). The digital image data is outputted from the radiation image detector 12 to the console 14 through the imaging control device 13.

The imaging control device 13 synchronizes the operations of the radiation source 11 and the radiation image detector 12 such that the accumulation operation of the radiation image detector 12 starts in synchronization with X-ray emission start timing of the radiation source 11, and the reading operation is performed in synchronization with the emission stop timing.

The radiation image detector 12 is provided with an exposure control device (not shown) for controlling exposure to the X-ray emitted from the radiation source 11. When the amount of exposure received by the radiation image detector 12 reaches a predetermined value, the exposure control device notifies the imaging control device 13. When the imaging control device 13 receives this notification, the imaging control device 13 sends the exposure stop signal to the high voltage generator 17 to stop the X-ray emission of the radiation source 11, even if a maximum exposure time has not been reached.

The maximum exposure time refers to the longest duration of a single exposure performed by the radiation source 11. Even if the emission amount or dose of the X-ray emitted from the radiation source 11 is unchanged, an X-ray transmission amount passing through the subject P varies with the body thickness of the subject P. The body thickness varies among individuals. Even the body thickness of the same person varies with a region. For this reason, the imaging control device 13 sets in the high voltage generator 17 the maximum exposure time determined based on the body thickness of the region surrounding the object of interest of the subject P.

Imaging conditions such as an object of interest (e.g. chest or abdomen), an X-ray tube voltage, and an X-ray tube current are inputted through the console 14, and set in the imaging control device 13. A numeral 18 indicates a body thickness measuring device 18 for measuring the body thickness of a region surrounding an object of interest (e.g. chest or abdomen) of the subject P. The imaging control device 13 calculates the maximum exposure time based on the set X-ray tube current and the body thickness measured by body thickness measuring device 18. The body thickness measuring device 18 transmits ultrasonic waves or laser to the object of interest of subject P, and then measures the body thickness based on the intensity of the echo waves or reflected laser, for example.

Alternatively, the body thickness may be set in the imaging control device 13 using the following methods. One method is to assume the body thickness from the weight and the height of the subject P. In the case where a body-weight measuring scale is provided in the patient table 15, the imaging control device 13 obtains the weight measured at the patient table 15. An approximate body thickness is calculated based on the obtained weight and the height of the subject P input through the console 14. Another method is to input the body thickness actually measured in advance through the console 14. Any of the above methods can be used for setting the body thickness.

A vital sign measuring device 19 is connected to the imaging control device 13. The vital sign measuring device 19 measures vital signs, e.g. cardiac cycles and respiration of the subject P. The vital sign measuring device 19 detects electrical signals generated in the heart muscle during alternate contraction and relaxation of the heart of the subject P through multiple electrodes attached to the body of the subject P, and then outputs in real time cardiac signals indicating conditions or statuses (contraction and relaxation phases) of cardiac cycles or heartbeats.

The vital sign measuring device 19 may output respiratory signals in real time. The respiratory signals indicate expansion and contraction of the lungs of the subject P. Impedance becomes high in the lung when air is breathed into the lung, which restricts or hinders the flow of AC current. Impedance becomes low in the lung when air is breathed out of the lung, which promotes the flow of the AC current. The vital sign measuring device 19 passes high-frequency AC current between multiple electrodes attached to the body of the subject P, and then detects changes in the impedance in the lungs between the breathing-in and the breathing-out of air. Thereby, the vital sign measuring device 19 outputs respiratory signals.

Figure 2:
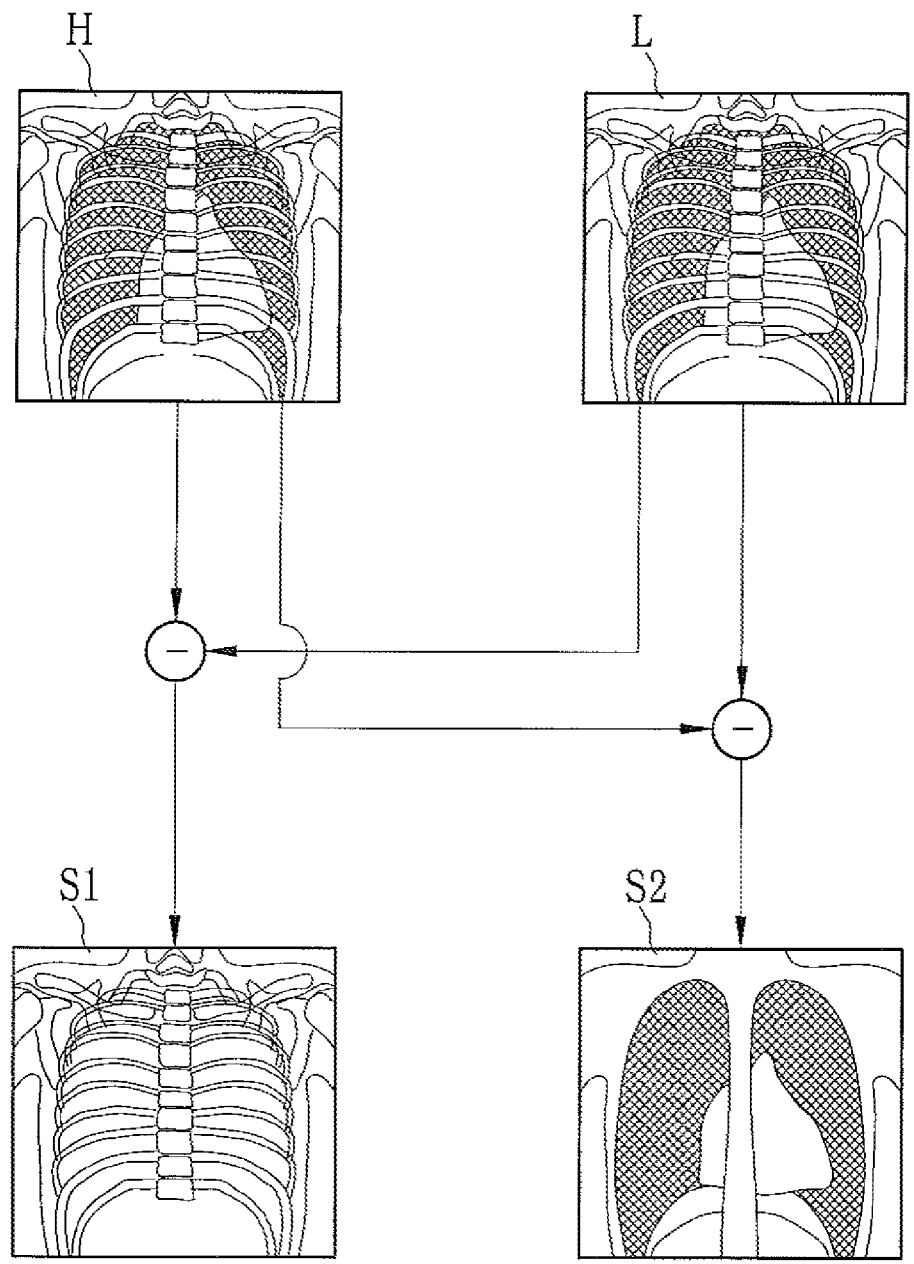
FIG. 2 is an explanatory view illustrating energy subtraction image processing.

In energy subtraction image processing, a low energy image L is subtracted from a high energy image H, and thus a subtracted image is obtained as shown in FIG. 2. The high and low energy images H and L are captured with two successive X-ray emissions, respectively. If the phase of the cardiac cycle of the heart in the high energy image H and the phase of the cardiac cycle of the heart in the low energy image L are different, for example, the heart in the relaxation phase is captured in the high energy image H and the heart in the contraction phase is captured in the low energy image L, a motion artifact is generated in the subtracted image due to the motion of the body of the subject P.

To reduce the motion artifact, the imaging control device 13 receives the cardiac signals and the respiratory signals from the vital sign measuring device 19 so as to control the radiation source 11 to match the phases of the cardiac cycle of the two sequential X-ray emissions with each other or to match the phases of the respiration of the two sequential X-ray emissions with each other.

A captured image is displayed on a monitor (not shown) of the console 14, which allows an operator to check whether the image has been captured successfully. When the image is captured successfully, the image is stored in an image server 20. Two radiation images (in this example, X-ray images) obtained at different energy levels, the high energy image H and the low energy image L, are stored in the image server 20 for the energy subtraction imaging.

The radiation image data outputted from the radiation image detector 12 is transferred to the console 14 via the imaging control device 13. The console 14 has an image processing function. The console 14 reads an image from the image server 20, and performs image processing for the energy subtraction. Alternatively, an image processing device other than the console 14, for example, an external terminal connected to the image server 20 via a communication network such as a LAN may be used for the image processing for the energy subtraction.

Referring to FIG. 2, the image processing for the energy subtraction is described using chest imaging as an example. Bones (e.g. backbone and ribs) and soft tissue (e.g. lungs) are recorded together in each of the high energy image H and the low energy image L. The bones and the soft tissue differ in X-ray energy absorption, namely, X-ray attenuation. Accordingly, a density ratio between the bones and the soft tissue of the high energy image H is different from that of the low energy image L.

To be more specific, in the high energy image H, a density ratio between the bones and the soft tissue becomes small. On the other hand, in the low energy image L, the density ratio between the bones and the soft tissue becomes large. This is because the soft tissue has relatively low absorption rates (high transmittance) of both the high and low energy components, and there is a small difference between the absorption rates of the high and low energy components. For the bones, conversely, there is a large difference between the absorption rates of the high and low energy components.

Image processing using the energy subtraction is based on the fact that the density ratios between the bones and the soft tissue differ between the high energy image H and the low energy image L. Two subtracted images, the bone part image S1 and the soft tissue image S2, are obtained using the following mathematical expressions (1) and (2).

$$\text{for the bone part image: } S1 = \alpha 1 \times H - \beta 1 \times L + B1 \qquad (1)$$

$$\text{for the soft tissue image: } S2 = \alpha 2 \times H - \beta 2 \times L + B2 \qquad (2)$$

For (1) and (2), each of α1, β1, α2, and β2 represents a weighting factor. Each of B1 and B2 represents a bias value.

To obtain the bone part image S1, the weighting factors α1 and β1 are determined for each of the high energy image H and the low energy image L to make the density of the soft tissue in the high energy image H and the density of the soft tissue in the low energy image L equal. When each of the high energy image H and the low energy image L is multiplied by the determined weighting factors α1 and β1, the density of the soft tissue in high energy image H and that in the low energy image L become equal. The energy subtraction of the two images makes the bone part image S1.

To obtain the soft tissue image S2, on the other hand, the weighting factors α2 and β2 are determined for each of the high energy image H and the low energy image L to make the density of the bones in the high energy image H and that in the low energy image L equal. When each of the high energy image H and the low energy image L is multiplied by the weighting factors α2 and β2, the density of the bones in high energy image H and that in the low energy image L become equal. The energy subtraction of the two images makes the soft tissue image S2.

In FIG. 1, a collimator (a movable aperture stop) 21 and a filter 22 are placed below the X-ray tube 16 of the radiation source 11. The collimator 21 limits an emission field of X-ray emitted from the X-ray tube 16. The filter 22 changes energy distribution of the emitted X-ray. The collimator 21 is, for example, a rectangular grid of lead (Pb) plates. Moving each lead plate adjusts the size of the opening area of the grid to pass through the X-ray.

Figure 3:
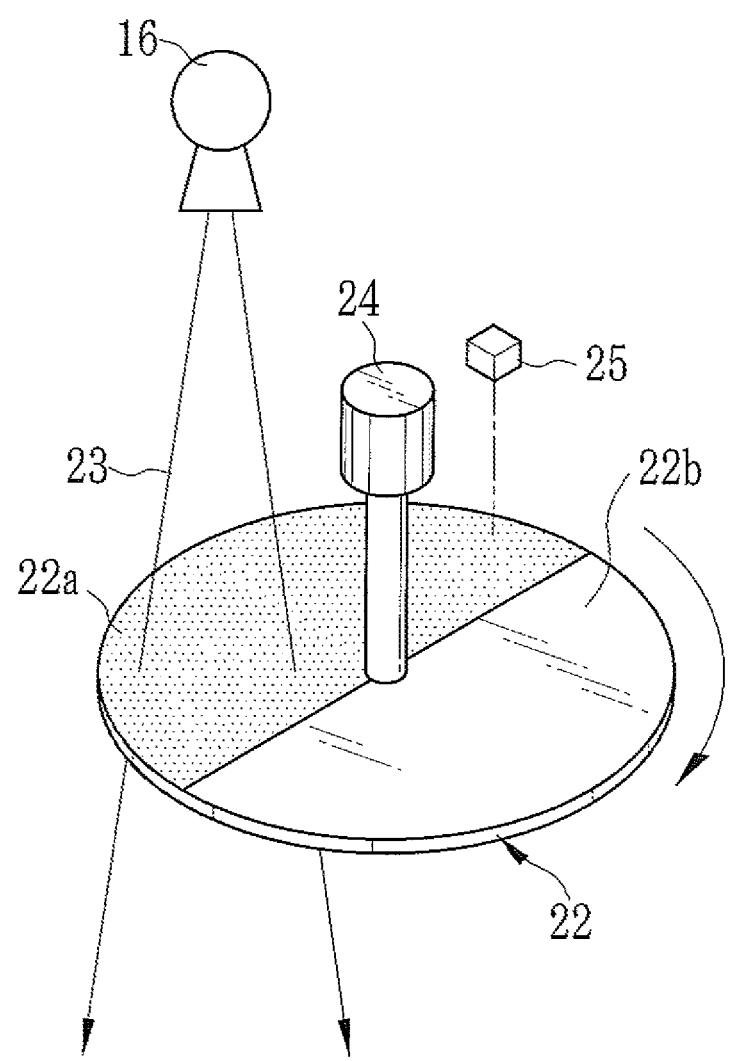
FIG. 3 is an explanatory view of a filter.

As shown in FIG. 3, the filter 22 is composed of a circular rotary plate as a base or substrate. On the surface of the rotary plate, two areas, a semi-circular filter area 22a and a transmission area 22b, are provided.

The filter area 22a is an area to which an X-ray absorbing material, e.g. copper (Cu) or gadolinium (Gd), is applied as a layer or coating. This X-ray absorbing material absorbs the low energy component of the X-ray. Thus, the filter area 22a cuts the low energy component of the X-ray emitted from the X-ray tube 16, but passes through the high energy component. The rotary plate is formed from a material with high X-ray transmission. On the other hand, the transmission area 22b is a through area without the application of the X-ray absorbing material and not having a filter function. A cutout or an opening formed in the rotary plate may also be used as the transmission area 22b.

The filter 22 is rotated or shifted such that the filter area 22a is alternately and periodically inserted and retracted from a path 23 of radiation (in this example, X-ray). Upon the retraction of the filter area 22a from the path 23, the transmission area 22b is inserted into the path 23. In other words, the filter area 22a and the transmission area 22b are alternately inserted and retracted from the path 23 of X-ray. A motor 24 is a driver to rotate or shift the filter 22. During the energy subtraction imaging, the motor 24 starts to rotate before the start of the first radiation emission (first X-ray emission) and keeps rotating at a constant speed until the end of the second radiation emission (second X-ray emission). The filter 22, driven by the motor 24, also rotates or shifts at a constant speed. As a result, an area shifting cycle or shift cycle to insert and retract the filter area 22a of the filter 22 from the path 23 also becomes constant.

A filter position detector 25 detects a rotational position of the filter 22. The filter position detector 25 is, for example, a photosensor for detecting a marker (not shown) on the filter 22. The filter position detector 25 outputs an ON signal while the filter area 22a is inserted into the path 23 of X-ray (radiation) and an OFF signal while the filter area 22a is retracted from the path 23. The ON and OFF signals outputted from the filter position detector 25 are inputted to the imaging control device 13.

The filter area 22a and the transmission area 22b are alternately inserted into the path 23 by the rotation of the filter 22. In accordance with the output signal (filter position detecting signal) from the filter position detector 25, the imaging control device 13 detects a phase of the filter 22, e.g. the timing for the filter area 22a to start entering the path 23, a time period in which the filter area 22a covers the entire path 23, the timings for the filter area 22a to retract from the path 23 and for the transmission area 22b to start entering the path 23.

Figure 4A:
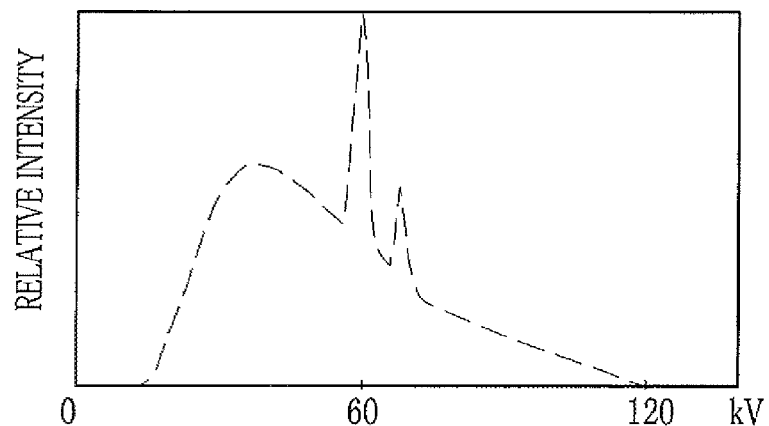
FIGS. 4A, 4B, and 4C are explanatory views illustrating energy distributions of radiations at two wavelengths and changes in the energy distributions with the use of a filter.
Figure 4B:
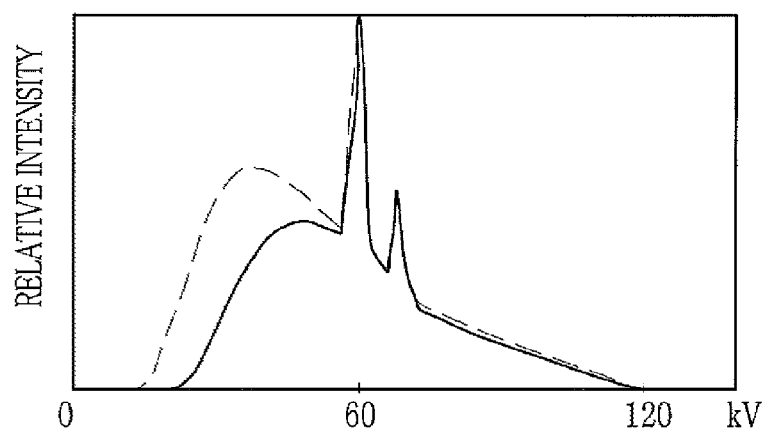
Figure 4C:
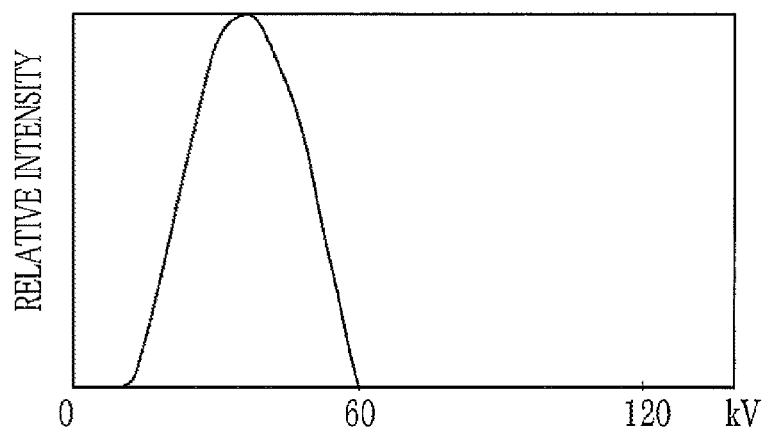

In each of FIGS. 4A to 4C, the horizontal axis indicates energy, and the vertical axis indicates relative intensity in each of the high and low energy components. The relative intensity is standardized with the maximum value of the radiation, in this case, X-ray of each energy distribution. The energy subtraction imaging is commonly used for chest images where lungs are mostly covered with ribs. For the energy subtraction imaging of the chest images, for example, X-rays of two different energy distributions, high-energy X-ray generated with the X-ray tube voltage of 120 kV (see FIG. 4A) and low-energy X-ray generated with the X-ray tube voltage of 60 kV (see FIG. 4C), are used.

As shown in FIG. 4A, peak energy of the high-energy X-ray is 120 kV. The peak energy and average energy of the high-energy X-ray are higher than those of the low-energy X-ray shown in FIG. 4C. As is well known, abruptly increasing portions close to the center of the energy distribution of the high-energy X-ray indicate characteristic X-rays. When an electron from an outer shell transfers to a vacancy, created by ejection of an electron in an inner shell, a difference in orbital energy between two electrons are released as characteristic X-rays or electromagnetic waves. Characteristic X-ray energy is specific to an element, and defined by a material of the target of the X-ray tube 16.

As shown in FIG. 4C, peak energy of the low-energy X-ray (60 kV) is 60 kV. The peak energy and average energy of the low-energy X-ray are lower than those of the high-energy X-ray. The energy distribution of the high-energy X-ray includes an energy component of equal to or less than 60 kV. Thus, the energy distribution of the high-energy X-ray and that of the low-energy X-ray are partly overlapped with each other.

The graph of FIG. 4B shows the energy distribution (solid lines) of the high-energy X-ray with the use of the filter 22, that is, the energy distribution of the high-energy X-ray passed through the filter area 22a, and the energy distribution (dotted lines) of the high-energy X-ray without the use of the filter 22, that is, the energy distribution of the high-energy X-ray not having been passed through the filter area 22a. The distribution of the high-energy X-ray without the use of the filter 22, depicted in dotted lines in FIG. 4B, is the same as the distribution shown in FIG. 4A. On the other hand, in the case where the filter 22 is used, as depicted in solid lines, the low energy component is cut down. With the use of the filter 22, an overlapping amount of the energy component of the low-energy X-ray and the energy component of high-energy X-ray is reduced, and thus the separation of the high-energy X-ray and the low-energy X-ray is improved.

Each graph shown in FIG. 4B is normalized with the maximum value of the energy distribution. Although the high energy components (with the use of the filter 22) depicted in solid lines and the high energy components (without the use of the filter 22) depicted in dotted lines have the same intensity regardless of the use of the filter 22, a part of the high energy component is actually cut down in addition to the low energy component with the use of the filter 22. As a result, the intensity of the high energy component (solid lines) is reduced with the use of the filter 22, compared to the intensity of the high energy component (dotted lines) without the use of the filter 22.

Figure 5:
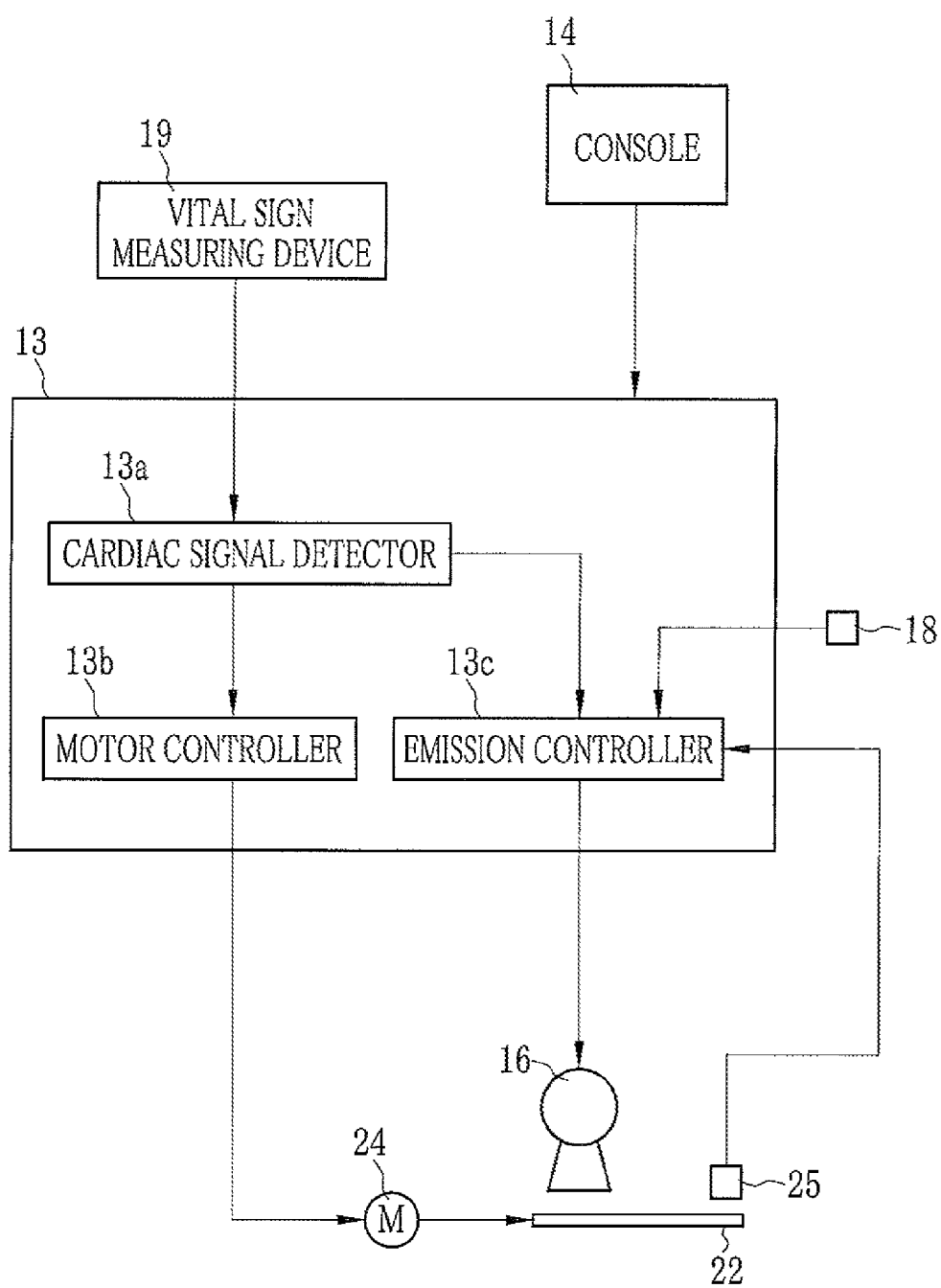
FIG. 5 is a schematic block diagram illustrating control configuration of an imaging control device.

As shown in FIG. 5, the imaging control device 13 is provided with a cardiac signal detector 13a, a motor controller 13b, and an emission controller 13c. The cardiac signal detector 13a detects cardiac signals outputted from the vital sign measuring device 19. The detected cardiac signals are outputted to the motor controller 13b.

The motor controller 13b determines the area shifting cycle or shift cycle of the filter 22 based on the cardiac signal. The motor controller 13b adjusts the drive speed (rotation speed) of the motor 24 so as to rotate the filter 22 at the determined area shifting cycle. Namely, the motor controller 13b determines the drive speed of the motor 24 to synchronize the area shifting cycle of the filter 22 with the cardiac cycle.

As shown in FIG. 6, the motor controller 13b determines the drive speed of the motor 24 based on the cardiac signal when, for example, imaging conditions inputted via the console 14 are set in the imaging control device 13, and starts rotating the motor 24 accordingly. The motor controller 13b rotates the motor 24 at the determined constant drive speed to rotate the filter 22 at a constant speed during the sequential two X-ray emissions, T1 and T2, in the energy subtraction imaging.

The area shifting cycle of the filter 22 synchronizes with the cardiac cycle (approximately 1 second). Accordingly, the filter area 22a and the transmission area 22b are alternately inserted into the path 23 of X-ray in each cardiac cycle or heartbeat while the motor 24 rotates.

The emission controller 13c controls the emission timing based on or in accordance with the filter position detecting signal and the cardiac signal. First, the emission controller 13c detects a phase of the filter 22, namely, the emission controller 13c detects whether the filter area 22a is inserted or retracted from the path 23 of X-ray based on the filter position detecting signal. To be more precise, after the instruction for imaging has been inputted, the emission controller 13c detects the rising edge of the filter position detecting signal to detect that the filter area 22a has started to enter the path 23.

In a single cardiac cycle, a P wave, a QRS complex, and a T wave appear. The P wave corresponds to the duration of the activation of atria. The QRS complex corresponds to the duration of the ventricular activation and the subsequent expansion and contraction of the ventricles. The T wave corresponds the duration of the contraction of the activated ventricles. During the T-P interval or a time period after the T-wave and before the next P wave, the heart is contracted and remains relatively stable.

After detecting the rising edge of filter position detecting signal, the emission controller 13c detects a phase of the cardiac cycle or heartbeat based on the cardiac signal. To be more precise, the emission controller 13c detects that the phase of the cardiac cycle is within the T-P interval where the heart is in a steady or stable state. When the phase of the cardiac cycle is within the T-P interval, the emission controller 13c outputs the exposure start signal for the first X-ray emission T1 of the high-energy X-ray. At this time, the filter area 22a has been inserted into the path 23 of X-ray. The high-energy X-ray passes through the filter area 22a so that the low energy component of the high-energy X-ray is absorbed by the filter area 22a. The high-energy X-ray passes through the subject P and reaches the radiation image detector 12.

After the first X-ray emission T1, the filter area 22a is retracted from the path 23, and the transmission area 22b is inserted into the path 23 for the next cardiac cycle. The emission controller 13c detects a falling edge of the filter position detecting signal, which indicates the retraction of the filter area 22a from the path 23. Then, the emission controller 13c detects the phase of the cardiac cycle is within the T-P interval, and outputs the exposure start signal for the second X-ray emission T2 of the low-energy X-ray. At this time, the transmission area 22b has been inserted into the path 23. The transmission area 22b allows the low-energy X-ray to pass therethrough without cutting its low energy component. Thus, the low-energy X-ray passes through the subject P and reaches the radiation image detector 12.

In this example, to control the emission timings, the emission controller 13c detects the phase of the filter 22 and the phase of the cardiac cycle in accordance with the filter position detecting signal and the cardiac signal, respectively. The area shifting cycle of the filter 22 and the cardiac cycle are previously synchronized before the start of the X-ray emission. Accordingly, the detection of one of the phases of the filter 22 and the cardiac cycle allows controlling the emission timing. For example, during the T-P interval in the cardiac signal, the phase of the filter 22 is synchronized with the phase of the cardiac cycle in order that the rising edge or the falling edge of the filter position detecting signal can be outputted. Thereby, the emission timing can be controlled only with the filter position detecting signal. Additionally, monitoring both the filter position detecting signal and the cardiac signal improves accuracy and safety of the emission timing control as described in the above example.

With referring to FIG. 7, an operation of the above configuration is described. To perform energy subtraction imaging, imaging conditions, e.g. an X-ray tube current, an X-ray tube voltage, and an object of interest are inputted through the console 14 to be set in the imaging control device 13 (S101). The imaging control device 13 calculates the maximum exposure time based on the object of interest and the body thickness inputted from the body thickness measuring device 18.

The cardiac signal detector 13a of the imaging control device 13 detects the cardiac signal from the vital sign measuring device 19, and then outputs the cardiac signal to the motor controller 13b. Based on or in accordance with the cardiac signal, the motor controller 13b determines the area shifting cycle of the filter 22 such that the area shifting cycle synchronizes with the cardiac cycle (S102). The drive speed of the motor 24 is determined to achieve the area shifting cycle. The motor controller 13b starts to rotate the motor 24 at the determined drive speed. Thus, the filter 22 starts to rotate (S103).

As shown in FIG. 6, when the instruction for imaging is inputted from the console 14 (S104), the emission controller 13c of the imaging control device 13 outputs two exposure start signals in sequence such that the phase of the filter 22, the phase of the cardiac cycle, and the emission timing are synchronized based on or in accordance with the filter position detecting signal and the cardiac signal. In accordance with the exposure start signal, the radiation source 11 performs two X-ray emissions, T1 with high-energy X-ray and T2 with low-energy X-ray (S105). After the two X-ray emissions, T1 and T2, are ended, the motor controller 13b stops the rotation of the motor 24, which stops the rotation of the filter 22 (S106).

In the radiation imaging apparatus 10 of the present invention, the filter 22 starts to rotate before the instruction for energy subtraction imaging is inputted, namely, the filter 22 starts to rotate before the first radiation emission or first X-ray emission T1. During the imaging until the end of the second radiation emission or second X-ray emission T2, the filter 22 rotates at the constant area shifting cycle or shift cycle. Accordingly, area shifting control which requires inputting of a pulse to shift the filter 22 is unnecessary during two X-ray emissions, T1 and T2. The radiation imaging apparatus 10 of the present invention eliminates the use of a high-performance filter switching device or filter controller which inputs a pulse in accordance with the exposure start signal outputted during imaging to switch filters as described in U.S. Pat. No. 7,636,413, incurring no additional device cost.

The radiation imaging apparatus 10 of the present invention is provided with a function to adjust the area shifting cycle of the filter 22 to synchronize it with the cardiac cycle. It is not necessary for the radiation imaging apparatus 10 of the present invention to wait for the timing at which the area shifting cycle and the cardiac cycle coincide each other after the first X-ray emission unlike the conventional imaging apparatus disclosed in Japanese Patent Laid-Open Publication No. 2003-210442. Accordingly, two X-ray emissions are performed over two successive cardiac cycles or heartbeats, which shorten the imaging time. As a result, physical burdens of the subject are reduced.

In the above embodiment, the cardiac signal is used as subject information, that is, information related to the subject, and the area shifting cycle or the shift cycle of the filter 22 is determined based on or in accordance with the cardiac signal by way of example. Alternatively, a respiratory signal may be used for determining the area shifting cycle of the filter 22. Respiration is periodic as with the cardiac cycle, and one breathes in and out repeatedly. In the case where the area shifting cycle of the filter 22 is determined based on the respiratory signal, the drive speed is determined so as to synchronize the area shifting cycle of the filter 22 with the respiratory cycle. The emission timing is synchronized with a phase of respiration such that two successive X-ray emissions are performed at the time when, for example, the subject breathed in fully with the lungs expanded to the maximum and is just about to breathe out. Thus, the motion artifact caused by breathing is prevented.

Respiration, unlike the cardiac cycle, can be temporarily controlled consciously. To prevent lung motion due to breathing during the X-ray imaging, it is common to instruct the subject P to fully breathe in and hold his/her breath with the lungs expanded. However, holding one's breath may be physically burdensome. If the subject P is a small child or infant, such instruction is difficult to follow. In such cases, it is particularly effective to synchronize the emission timings with the phases of the respiration to control the emission timings.

Figure 8A:
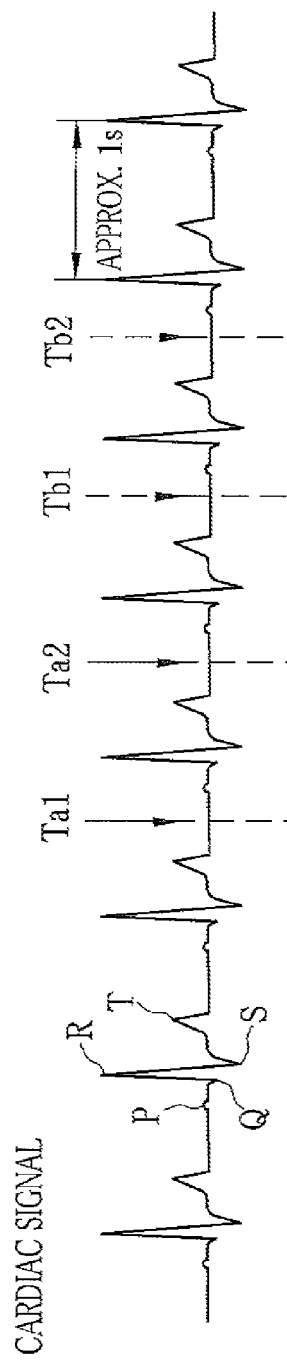
FIG. 8 is an explanatory view of an example in which exposure timings are synchronized to a cardiac cycle and respiration.
Figure 8B:
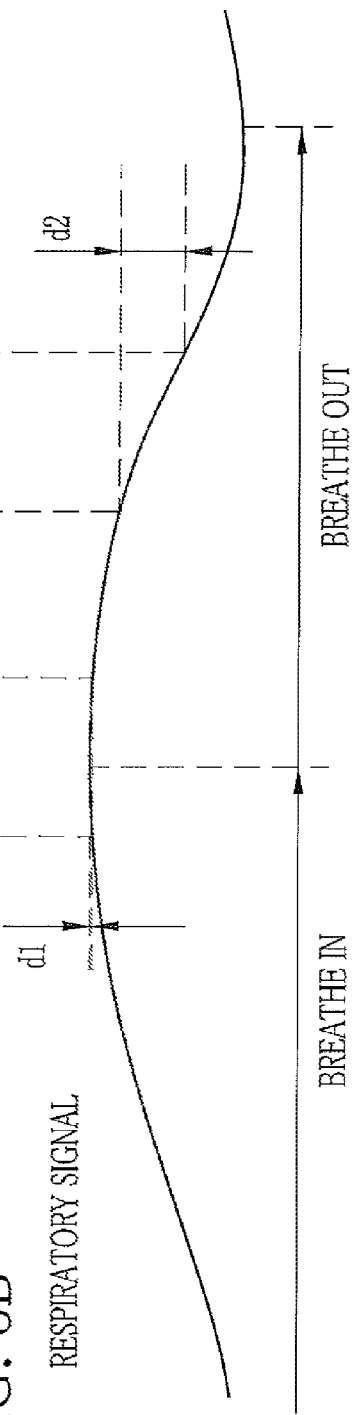

As shown in FIGS. 8A and 8B, in addition to the synchronization between the emission timing and the phase of the cardiac cycle, the X-ray emission may be performed at the timing synchronized with a phase of the respiration where lung motion is small. In FIGS. 8A and 8B, two successive X-ray emissions (Ta1 and Ta2) performed at around the time when the subject breathed in fully with the lungs expanded and two successive X-ray emissions (Tb1 and Tb2) performed during the breathing out are compared. An amount d1 indicating an amount of change in the size of lungs between Ta1 and Ta2 is smaller than an amount d2 indicating an amount of change in the size of lungs between Tb1 and Tb2. Performing the X-ray emissions at the timings of Ta1 and Ta2 reduces motion artifact due to respiration.

In the above first embodiment, the first and second X-ray emissions are performed in the two successive cardiac cycles, respectively. Alternatively, as shown in FIG. 9, two X-ray emissions, T1 and T2, may be performed within one cardiac cycle. The cardiac cycle is of approximately 1 second on average. The radiation source 11 is capable of sequentially emitting X-rays at an interval in a range from approximately 100 milliseconds (abbreviated as ms) to 200 ms, so that two X-ray emissions can be performed within one cardiac cycle. In this case, the area shifting cycle or shift cycle is determined such that the filter area 22a is inserted and retracted from the path of the X-ray within one cardiac cycle. In order to prevent body motion during imaging, it is preferable to determine the area shifting cycle to remain within the T-P interval where the heart is in a relatively steady state. Thereby, two X-ray emissions, T1 and T2, are performed within the T-P interval, preventing the motion artifact.

In the above first embodiment, the filter 22 having one type of the filter area 22a and the transmission area 22b is described as an example. Instead of the transmission area 22b, a second filter area different from the filter area 22a may be provided. This second filter area cuts the high energy component of the energy distribution like a K-edge filter or K-edge absorption filter disclosed in Japanese Patent Laid-Open Publication No. 5-27043. The low energy component of the high-energy X-ray is cut with the filter area 22a, and the high energy component of the low-energy X-ray is cut with the second filter area. Thus, addition of the second filter area improves the separation of the high-energy X-ray and the low-energy X-ray.

The filter 22 may be provided with three or more filter areas. In this case, two of the three filter areas are selected for the X-rays of two different energy distributions. The area shifting cycle or the shift cycle of the filter 22 is determined such that the selected two filter areas are inserted into the path of the X-ray based on the cardiac cycle and/or the respiratory cycle. Alternatively, the X-rays of three or more different energy distributions may be emitted in sequence for the energy subtraction imaging as described in, for example, Japanese Patent Laid-Open Publication No. 2009-78035. In this case, the area shifting cycle of the filter is determined such that three or more filter areas formed on the filter is selectively inserted in sequence into the path of the X-ray based on the cardiac cycle.

In the above example, the filter 22 is used as an energy separation filter for blocking a high or low energy component of X-rays. Alternatively, X-ray of the same X-ray tube voltage may be emitted twice, for example, and the filter 22 is used for one of the X-ray emissions to generate X-rays of two different energy distributions. Thus, the filter 22 can be used for generating X-rays of different energy distributions in addition to the use as the energy separation filter.

Figure 10:
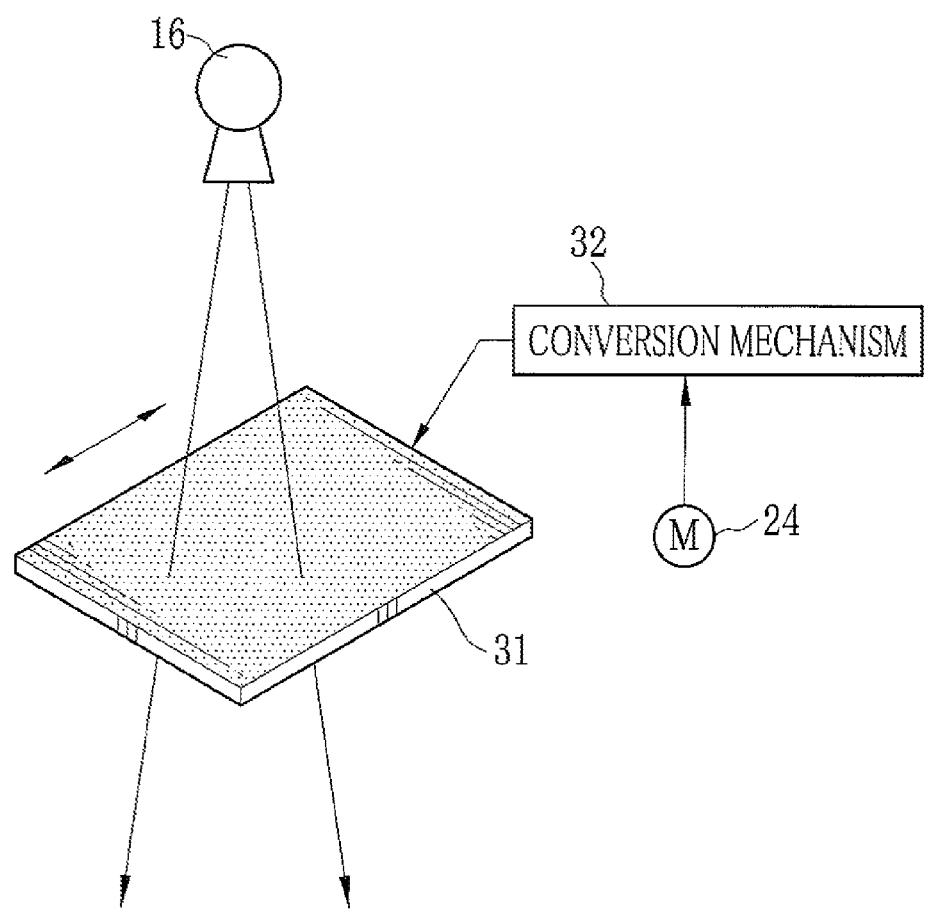
FIG. 10 is an explanatory view of a linearly moving filter.

In the above example, the rotary filter is described as an example. Alternatively or in addition, as shown in FIG. 10, a filter 31 that linearly reciprocates may be used. The filter 31 is, for example, rectangular in shape, and provided with a layer or coating as a filter area on a substrate of the filter 31. The filter 31 is movable between an insert position where the filter 31 is inserted into the path 23 of X-ray and a retract position where the filter 31 is retracted from the path 23. A conversion mechanism 32 converts rotary motion of the motor 24 into linear reciprocal motion of the filter 31. The conversion mechanism 32 is composed of, for example, a spring and a cam. The spring biases the filter 31 against the retract position and the cam presses the filter 31 into the inserted position against the bias of the spring. Thus, the rotary motion of the motor 24 is converted into the linear motion of the filter 31.

A motor is described as an example of a driver. Alternatively, an actuator other than the motor, e.g. a solenoid may be used as the driver as long as it is capable of shifting or moving the filter at a predetermined area shifting cycle or shift cycle.

Figures 11, 12:
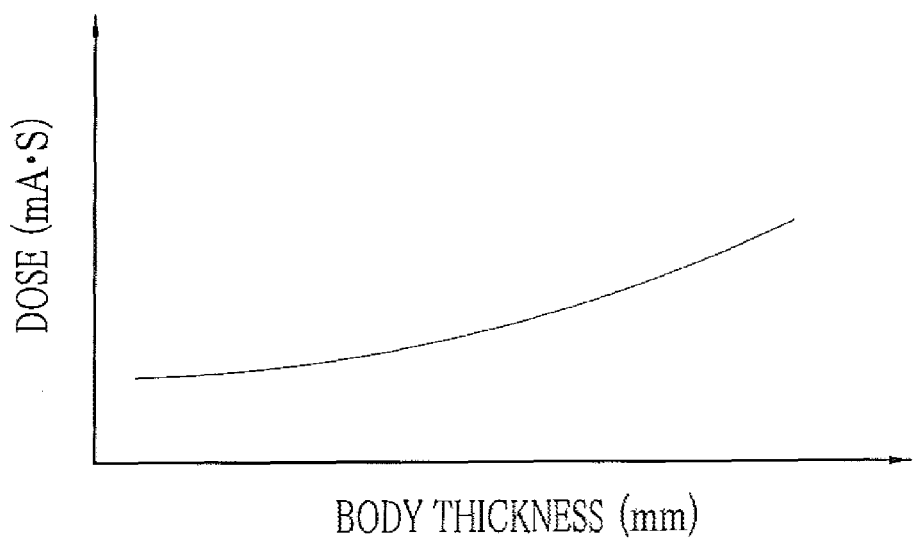
FIG. 11 is a graph showing a relation between body thickness and dose.
FIG. 12 is an explanatory view of combinations of a radiation tube current and dose.

As described above, the X-ray transmission amount varies according to the body thickness even if the dose of the X-ray emission from the radiation source 11 is unchanged. To obtain an appropriate dose, the X-ray tube current and the maximum exposure time are set in accordance with the body thickness. In FIG. 11, the horizontal axis represents the body thickness, and the vertical axis represents the dose. As shown in FIG. 11, as the body thickness increases, the required dose increases. The dose is a product (unit: mAs) of an X-ray tube current (unit: mA) and the X-ray emission time or exposure time (unit: s). As shown in the combinations 1 to 3 in FIG. 12, there are various combinations of the X-ray tube current and the X-ray emission time to obtain the same dose.

The imaging control device 13 has a memory in which table information indicating the relations between the body thickness and the dose as shown in FIG. 11 and table information indicating combinations of the X-ray tube current and the X-ray emission time as shown in FIG. 12 are stored. With referring to the table information, a required dose is retrieved in accordance with the body thickness, and then an appropriate combination of the X-ray tube current and the X-ray emission time for the retrieved dose is selected.

In the above example, the imaging control device 13 sets the maximum exposure time such that it remains within one cardiac cycle, more preferably, within a T-P interval in one cardiac cycle. To be more specific, the imaging control device 13 selects a combination of an X-ray tube current and an X-ray emission time from the table information of the combinations shown in the FIG. 12 such that the X-ray emission time of the selected combination remains within one cardiac cycle.

For example, the table information contains multiple combinations of X-ray emission time and X-ray tube current, and the X-ray emission time remains within one cardiac cycle in some of the combinations while the X-ray emission time exceeds one cardiac cycle in other combinations. In this case, the imaging control device 13 selects the combination with the X-ray emission time within one cardiac cycle.

A subject may have the body thickness higher-than-average, which may require the dose of higher-than-average. In that case, a suitable combination may not be contained in the previously prepared table information. In this case, the imaging control device 13 sets the maximum exposure time which remains within one cardiac cycle, and then calculates the X-ray tube current to obtain the required dose with the set maximum exposure time.

Alternatively, the required dose may be obtained with multiple X-ray exposures over multiple cardiac cycles. For example, in the case where the maximum exposure time determined in accordance with the body thickness is 0.08 seconds, the X-ray exposure of 0.04 seconds is allocated to each of the two cardiac cycles. Thus, the maximum exposure time is 0.08 seconds in total over two cardiac cycles.

In this case, the radiation source 11 operates as follows. To perform high-energy X-ray emission T1, the radiation source 11 performs X-ray emission T1 for 0.04 s within the first cardiac cycle in which the filter area 22a is inserted into the path 23. Thereafter, the radiation source 11 temporarily stops the X-ray emission T1, and then resumes the X-ray emission T1 in the second cardiac cycle when the filter area 22a is inserted into the path 23 again and performs the remaining X-ray emission T1 for 0.04 s. After the high-energy X-ray emission T1 is ended, the low-energy X-ray emission T2 is performed twice over two cardiac cycles with the transmission area 22b being inserted into the path 23.

Allocating the X-ray emission time to multiple cardiac cycles is effective in the case where the highest X-ray tube current is limited, and the X-ray emission time for obtaining the required dose exceeds the cardiac cycle.

Second Embodiment

In the first embodiment, the cardiac cycle and respiration are used as examples of the subject information. Alternatively, the body thickness may be used as the subject information. In this case, the area shifting cycle or shift cycle of the filter 22 may be determined in consideration of the body thickness. In other words, the imaging control device 13 determines the area shifting cycle of the filter 22 in accordance with the maximum exposure time determined based on the body thickness, regardless of the cardiac cycle or respiratory cycle.

For the energy subtraction imaging, the imaging control device 13 obtains the imaging time required for the two successive X-ray emissions, T1 and T2, based on or in accordance with the maximum exposure time. For example, in the case where the maximum exposure time for each of the high-energy X-ray emission T1 and the low-energy X-ray emission T2 is 0.08 seconds, the total maximum exposure time is 0.16 seconds. To calculate the imaging time, an interval time between the two X-ray emissions, T1 and T2, is added to the total maximum exposure time. The motor controller 13b determines the area shifting cycle based on the calculated imaging time, and determines the driving speed of the motor 24 in accordance with the area shifting cycle.

To obtain the maximum exposure time, there are, for example, two ways of thinking. One is aimed to reduce an influence (motion artifact) caused by body motion of the subject P. To reduce the motion artifact, shorter maximum exposure time is the better. Accordingly, the maximum exposure time is set as short as possible, and then the X-ray tube current is calculated to obtain the required dose.

The other is aimed for durability of the X-ray tube 16 and the high voltage generator 17. As shown in FIGS. 11 and 12, the dose is a product of the X-ray emission time (exposure time) and the X-ray tube current. The shorter the X-ray emission time, the larger the X-ray tube current becomes. However, if the X-ray tube current is too large, the durability of the X-ray tube 16 and the high voltage generator 17 decreases, e.g. the target of the X-ray tube 16 deteriorates due to thermal damage. To aim for the durability of the X-ray tube 16 and the high voltage generator 17, the low X-ray tube current is used with the extended the maximum exposure time. Each of the two ways of thinking has advantages and disadvantages. An aim in obtaining the maximum exposure time may change depending on the subject. It is preferable that a user can select the way of determining the maximum exposure time depending on the aim.

In this case, the imaging control device 13 is provided with two modes, a first calculation mode and a second calculation mode. The first calculation mode is aimed to reduce the motion artifact. The second calculation mode is aimed for the durability of the X-ray tube 16 and the high voltage generator 17. One of these modes is selected through the console 14. The table information shown in FIG. 12 is stored in the memory of the imaging control device 13.

In the case where the first calculation mode is selected, the imaging control device 13 selects from the table information a combination of an X-ray tube current and a relatively short X-ray emission time to achieve the required dose which is determined based on the body thickness. On the other hand, in the case where the second calculation mode is selected, the imaging control device 13 selects from the table information a combination of a relatively small X-ray tube current and an X-ray emission time to achieve the required dose which is determined based on the body thickness.

In addition to the first calculation mode and the second calculation mode, a third calculation mode may be used. In the third calculation mode, the maximum exposure time is calculated in consideration of both the reduction of the motion artifact and the durability of the X-ray tube 16 and the high voltage generator 17. In the third calculation mode, for example, a combination of the X-ray tube current of medium amount and the X-ray emission time of medium length is selected from among the combinations for obtaining the required dose.

In the above second embodiment, as an example, the body thickness is used as the subject information instead of the heartbeat and respiration, and the area shifting cycle of the filter 22 is determined based on the maximum exposure time in accordance with the body thickness. This second embodiment can be combined with an example of the first embodiment shown in FIG. 9 where two X-ray emissions are performed within one heartbeat. In other words, the area shifting cycle of the filter 22 can be determined using both the heartbeat and the body thickness as the subject information.

To be more specific, the cardiac cycle is obtained based on the cardiac signal, and then the area shifting cycle of the filter 22 is determined within one cardiac cycle in consideration of the maximum exposure time determined based on the body thickness.

Third Embodiment

Figure 13:
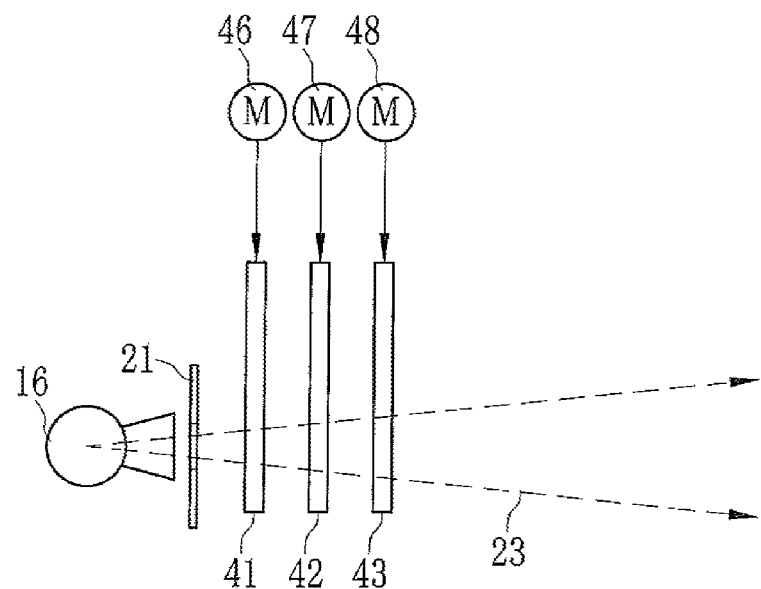
FIG. 13 is an explanatory view of a filter set having multiple filters.
Figure 14:
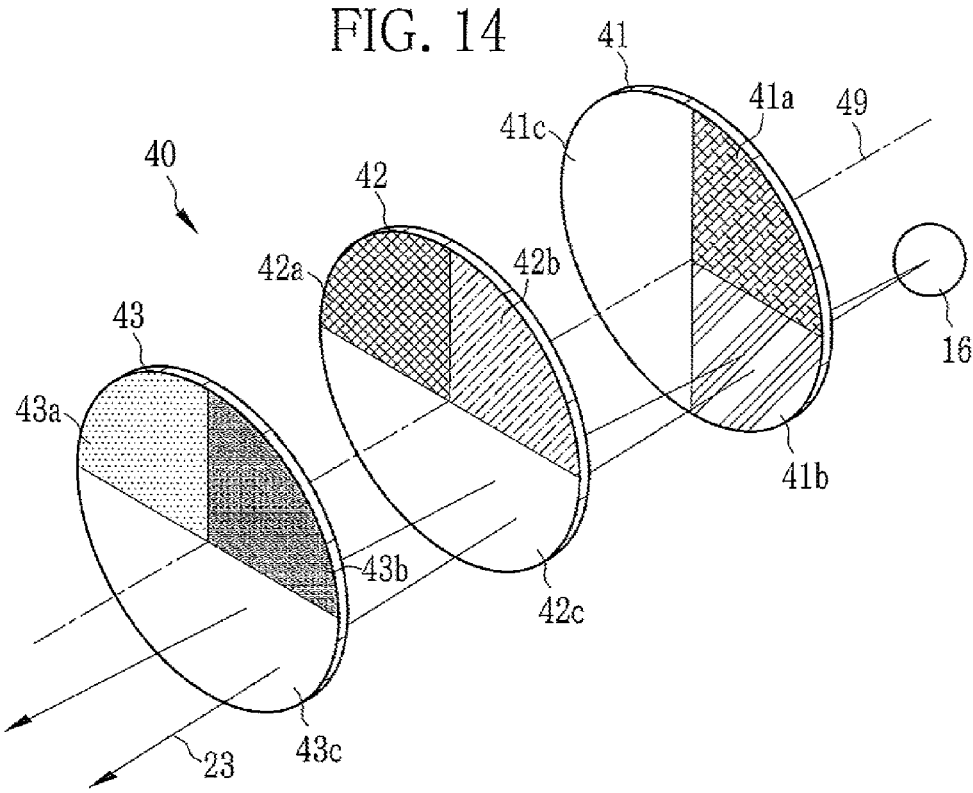
FIG. 14 is a perspective view of the filter set.

In the above embodiment, the filter, that is, a rotary plate is used as an example. In addition, a filter set 40 composed of multiple rotary plates may be used as shown in FIG. 13. The filter set 40 is composed of three filters 41 to 43. The filters 41 to 43 are composed of the rotation axes and motors 46 to 48, respectively, such that each of the filters 41 to 43 rotates individually with a predetermined area shifting cycle or shift cycle. As shown in FIG. 14, rotation centers of the filters 41 to 43 are respectively located on a line 49.

The filter 41 has two different filter areas 41a and 41b each located in a quadrant area of a circular rotary plate, and a transmission area 41c formed in a remaining semi-circular area thereof. A filter 42 has two different filter areas 42a and 42b each located in a quadrant area of a circular rotary plate, and a transmission area 42c formed in a remaining semi-circular area thereof. The filter 43 has two different filter areas 43a and 43b each located in a quadrant area of a circular rotary plate, and a transmission area 43c formed in a remaining semi-circular area thereof. A different layer or coating is formed on each of the filter areas 41a, 41b, 42a, 42b, 43a, and 43b.

As shown in FIG. 14, in the case where a filter, for example, the filter 41 is used, the transmission areas 42c and 43c of the filters 42 and 43 are inserted into the path 23. Similarly, in the case where the filter 42 or the filter 43 is used, the transmission areas of the filters not being used are inserted into the path 23.

There are various layers or coatings used for the filter areas, which differ in radiation (for example, X-ray) absorption properties. In addition to copper (Cu) and gadolinium (Gd) used in the above example, there are coatings composed of aluminum (Al), molybdenum (Mo), or rhodium (Rh). The radiation absorption properties vary among the coatings made from the same material depending on the thickness thereof.

The filter area with filter layers or coatings may be selected in accordance with an object of interest, e.g. abdomen, chest, or breast. In the case where the subject P is a small child, which requires minimum radiation exposure, the filter areas with coatings capable of cutting substantially entire range of radiation energies in addition to specific energy components are used.

Using the filter set 40 increases the kinds of the available filter areas with various coatings than in the case of using just one filter. With the increased choices, the filter areas can be selected in accordance with various purposes. In addition, the already attached multiple filters save an operator time and trouble of changing the filter compared to an apparatus having just one filter.

The filter set 40 can be used for the energy subtraction imaging described in the above first to the third embodiments. In addition, the filter set 40 can be used for imaging other than the energy subtraction imaging.

In the case where the filter set 40 is used, the filter areas are previously associated with imaging menus which are selectable using the console 14, respectively. In other words, when an imaging menu is selected using the console 14, a filter area previously associated with the selected imaging menu is used. For example, a filter area with a coating to cut low energy radiation is associated with the imaging menu for small children as the subjects, trading off image contrast for reduced exposure. On the other hand, a filter area with a coating which cuts a smaller amount of low energy radiation compared to the filter area for the small children is associated with the imaging menu for adults as the subjects. Thus, sufficient exposure for sharp radiation image is obtained. The console 14 is provided with a memory in which the imaging menus and the coated filter areas are associated with each other and stored.

After the imaging menu is selected, the console 14 reads from the memory the information of the filter area with the coating corresponding to the selected imaging menu, and sends the information to the imaging control device 13. The imaging control device 13 sends a control signal to the radiation source 11 so as to insert the filter area corresponding to the received information into the path 23 of radiation, for example, X-ray. The radiation source 11 drives the motors 46 to 48 to insert the filter area with the selected coating into the path 23, and shifts the filters with filter areas of unnecessary coatings to retract the filter areas and insert the transmission areas thereof to the path 23.

The following invention can be understood with the configuration of this embodiment. An imaging apparatus is provided with multiple filters selectably used and each having at least one kind of filter area. Each filter has a disc-shape, and the rotation axes of the filters are arranged along a straight line, and each filter can be rotated individually. It is preferable that each filter is provided with a transmission area (through area). When a filter area of a selected or associated filter is inserted into a radiation path, the transmission areas of the remaining filters are inserted into the path to retract the filter areas of the remaining filters from the path. It is preferable that the filter is selected in accordance with an imaging menu selected using a console.

The present invention may be applied to an apparatus using X-rays as the radiation. Alternatively, the present invention may be applied to an apparatus using radiation other than X-rays such as gamma rays and megavoltage X-rays for radiation therapy.

Various changes and modifications are possible in the present invention and may be understood to be within the present invention.

What is claimed is:

1. A radiation imaging apparatus comprising:
a radiation source for performing multiple radiation emissions to a subject;
a filter having at least one filter area for changing energy distribution of radiation in at least one of the multiple radiation emissions, the filter periodically shifting between an inserted state in which the at least one filter area is inserted in a path of radiation and a retracted state in which the at least one filter area is retracted from the path;
a cycle determining section for determining a shift cycle of the filter for shifting the at least one filter area between the inserted state and the retracted state before a start of the first radiation emission based on subject information;
a driver for driving the filter to shift at the determined shift cycle, the driver driving the filter to start shifting before a start of the first radiation emission and to shift until an end of the last radiation emission after the first radiation emission; and
an emission controller for outputting a signal for starting a radiation emission to the radiation source to control emission timing of radiation,
wherein the subject information includes cardiac cycle information and respiration information of the subject, and the radiation imaging apparatus further includes a signal detector for detecting a cardiac signal indicating a state of the cardiac cycle information and a respiratory signal indicating a state of the respiration information, and
wherein the cycle determining section determines the shift cycle so as to be in synchronization with the cardiac cycle information, and the emission controller synchronizes the emission timing with a phase of the respiration based on the respiratory signal.

2. The radiation imaging apparatus of claim 1, further including a filter phase detector for detecting a phase of the filter, and the emission controller synchronizes the emission timing with the phase of the filter.

3. The radiation imaging apparatus of claim 1, wherein the filter includes multiple filter areas and the multiple filter areas are selectively inserted in sequence into the path.

4. The radiation imaging apparatus of claim 1, wherein the filter includes multiple filters each having at least one filter area, and the multiple filters are selectably used.

5. The radiation imaging apparatus of claim 4, wherein each of the multiple filters is individually rotatable, and arranged to be insertable into the path, and has a transmission area for retracting the at least one filter area of the filter from the path when the at least one filter area of another filter is inserted in the path.

6. A radiation imaging apparatus comprising:
a radiation source for performing multiple radiation emissions to a subject;
a filter having at least one filter area for changing energy distribution of radiation in at least one of the multiple radiation emissions, the filter periodically shifting between an inserted state in which the at least one filter area is inserted in a path of radiation and a retracted state in which the at least one filter area is retracted from the path;
a cycle determining section for determining a shift cycle of the filter for shifting the at least one filter area between the inserted state and the retracted state based on subject information; and
a driver for driving the filter to shift at the determined shift cycle, the driver driving the filter to start shifting before a start of the first radiation emission and to shift until an end of the last radiation emission after the first radiation emission, wherein the subject information is body thickness of the subject, and the cycle determining section determines the shift cycle in accordance with a maximum exposure time determined based on the body thickness.

7. An imaging control device for controlling a radiation source for performing multiple radiation emissions to a subject, and a filter having at least one filter area for changing energy distribution of radiation in at least one of the multiple radiation emissions, the filter periodically shifting between an inserted state in which the at least one filter area is inserted in a path of radiation and a retracted state in which the at least one filter area is retracted from the path, the imaging control device comprising:
a cycle determining section for determining a shift cycle of the filter for shifting the at least one filter area between the inserted state and the retracted state before a start of the first radiation emission based on subject information;
a controller for controlling a driver for driving the filter, the controller controlling the driver to shift the filter at the determined shift cycle by starting before a start of the first radiation emission and until an end of the last radiation emission after the first radiation emission; and
an emission controller for outputting a signal for starting a radiation emission to the radiation source to control emission timing of radiation,
wherein the subject information includes cardiac cycle information and respiration information of the subject, and the radiation imaging apparatus further includes a signal detector for detecting a cardiac signal indicating a state of the cardiac cycle information and a respiratory signal indicating a state of the respiration information, and
wherein the cycle determining section determines the shift cycle so as to be in synchronization with the cardiac cycle information, and the emission controller synchronizes the emission timing with a phase of the respiration based on the respiratory signal.

* * * * *